(12) United States Patent
Acosta

(10) Patent No.: US 11,399,974 B2
(45) Date of Patent: Aug. 2, 2022

(54) URINE COLLECTION APPARATUSES

(71) Applicant: ACOSTA MEDICAL GROUP, INC., Humble, TX (US)

(72) Inventor: Fred Acosta, Humble, TX (US)

(73) Assignee: Acosta Medical Group, Houston, TX (US)

( * ) Notice: Subject to any disclaimer, the term of this patent is extended or adjusted under 35 U.S.C. 154(b) by 20 days.

(21) Appl. No.: 17/084,313

(22) Filed: Oct. 29, 2020

(65) Prior Publication Data
US 2021/0186746 A1 Jun. 24, 2021

Related U.S. Application Data

(63) Continuation-in-part of application No. 16/816,734, filed on Mar. 12, 2020, and a continuation of application No. 16/387,069, filed on Apr. 17, 2019, said application No. 16/816,734 is a continuation of
(Continued)

(51) Int. Cl.
| | |
|---|---|
| *A61F 5/451* | (2006.01) |
| *A61F 5/44* | (2006.01) |
| *A61B 10/00* | (2006.01) |
| *A61B 5/145* | (2006.01) |
| *A61B 5/15* | (2006.01) |

(52) U.S. Cl.
CPC ............ *A61F 5/451* (2013.01); *A61F 5/4404* (2013.01); *A61B 5/14* (2013.01); *A61B 5/150992* (2013.01); *A61B 10/007* (2013.01); *A61B 10/0038* (2013.01)

(58) Field of Classification Search
CPC ........ A61F 5/451; A61F 5/4404; A61F 5/453; A61F 5/455; A61F 5/449; A61F 5/445; A61F 5/443; A61F 5/4405; A61F 5/4408; A61F 5/44; A61B 5/14; A61B 5/150992; A61B 10/0038; A61B 10/007; A61B 5/150366; A61B 5/150221; A61B 5/150045; A61B 10/0045; A61B 2010/008
See application file for complete search history.

(56) References Cited

U.S. PATENT DOCUMENTS

| | | | | |
|---|---|---|---|---|
| 3,559,651 A | * | 2/1971 | Moss ...................... | A61F 5/453 604/349 |
| 5,797,890 A | * | 8/1998 | Goulter ................... | A61F 5/453 604/351 |

(Continued)

*Primary Examiner* — Philip R Wiest
*Assistant Examiner* — Gregory J Feulner
(74) *Attorney, Agent, or Firm* — Hunton Andrews Kurth LLP

(57) ABSTRACT

The urine collection device is designed to be attached to a drain tube. The device may include a base secured to the pelvic area of a wearer, the base having a central opening. Connected to the base is a sheath. The central opening and the sheath can have complementary attachment components whereby the sheath may be attached to the base. The sheath includes an opening and attaches to a drain tube. A second sheath may be disposed outboard of the first sheath and secured to the base in a similar manner. In some embodiments the drain tube may be connected and disconnected from the sheath or sheaths without disturbing the installation of the device. One or more check valves may be included for assuring one-way flow in the drain tube.

20 Claims, 15 Drawing Sheets

Related U.S. Application Data application No. 14/995,672, filed on Jan. 14, 2016, now Pat. No. 10,588,775.

(60) Provisional application No. 62/927,360, filed on Oct. 29, 2019, provisional application No. 62/770,031, filed on Nov. 20, 2018, provisional application No. 62/658,793, filed on Apr. 17, 2018.

(56) References Cited

U.S. PATENT DOCUMENTS

| | | | |
|---|---|---|---|
| 2004/0006321 A1* | 1/2004 | Cheng | A61F 5/44 604/349 |
| 2005/0177133 A1* | 8/2005 | Nielsen | A61L 29/06 604/544 |
| 2012/0316522 A1* | 12/2012 | Carter | A61F 5/449 604/353 |
| 2013/0053804 A1* | 2/2013 | Sorensen | A61F 5/453 604/349 |

* cited by examiner

URINE COLLECTION APPARATUSES

CROSS-REFERENCE TO RELATED APPLICATIONS

The present invention is a continuation-in-part of U.S. application Ser. No. 16/816,734, filed Mar. 12, 2020 which is a continuation of U.S. application Ser. No. 14/995,672 filed Jan. 14, 2016 which issued as U.S. Pat. No. 10,588,775. The present invention also claims priority to U.S. application Ser. No. 16/387,069, filed Apr. 17, 2019 which claims priority to U.S. provisional application 62/658,793 filed Apr. 17, 2018 and U.S. provisional application No. 62/770,031 filed Nov. 20, 2018 all of which are incorporated by reference. The present application also claims priority to U.S. Provisional Application No. 62/927,360 filed Oct. 29, 2019.

FIELD OF THE INVENTION

This invention is related to urine collection devices and is specifically directed to male catheters.

BACKGROUND AND SUMMARY OF THE INVENTION

Historically, external male urinary catheters were generally retained on a penis with an adhesive tape or similar pressure sensitive adhesive means, whereby the catheter could be readily attached by applying pressure to the adhesive bearing area of the catheter and securing it to the penis. Self-sealing catheters which do not require an adhesive have been more recently developed, as well. Both adhesive and self-sealing external catheters are difficult to apply, especially to males having a recessive penis.

The strapless catheters on the market have the adhesive sandwiched between successive rolls of the catheter. As the catheter is unrolled, the inner surface comes into contact with the penile surface ad is then pressed to seal. The sealing surface is generally located on the shaft, behind the glans.

A glans cap catheter is also available and is shaped like a cup to fit only over the glans. This has been generally unsuccessful because a glans-only seal does not withstand body movement and urine pressure unless an aggressive adhesive is used. This generally can cause pain and damage during removal.

A more recent condom catheter is shown in U.S. Pat. No. 5,334,175, issued on Aug. 2, 1994 to Conway, et al. This catheter includes a section which can conform to the shape of the penile tip and to adhere to it. The catheter can be unrolled onto and adhere to the penile shaft. The opposite end can be pulled into an elongated tube which serves as a urine collector.

Another example of a condom style catheter is shown and described in U.S. Pat. No. 4,626,250, issued on Dec. 2, 1986 to Schneider. This external catheter includes an adhesive element mounted on the shaft of the penis with the catheter being adhesively applied to the adhesive element by placing the catheter over the glans and then unrolling the adhesive portion onto the adhesive element.

All of the prior art devices have drawbacks in that they are hard to apply, especially with a recessive penis, can cause pain and injury when removed from the shaft, and have tendency to leak. In addition, such products may also be ill-fitting, uncomfortable, unattractive, and/or present problems such as leakage, rashes, or other skin irritations.

What is needed is a urine collection device that is suitable for males, is potentially reusable, and/or avoids one or more of the aforementioned disadvantages. Thus, there remains a need for an external male catheter that is secure once applied, minimizes pain and injury to the penis, and is virtually leak proof.

Advantageously, the devices of the present application meet one or more of the aforementioned needs.

The subject invention eliminates the shortcomings of the prior art external male catheters by moving the attachment element from the penis to the pelvic area and providing a tube which loosely envelopes the penis with a release tube extending form the penis tube and into a drain bag. The drain bag and/or release tube may be detachably connected to the penis tube with a clip or similar means. This permits the catheter to be emptied without removing any portion of the collection elements of the catheter.

The external male catheter of the subject invention is designed to be attached to a drain tube of a standard catheter, with the catheter being non-invasive of the penis. The catheter includes a base secured to the pelvic area of a wearer, the base having a central opening for accommodating a penis. Connected to the base is a sheath for housing the penis, one end of the sheath adjacent the base and a second end of the sheath extending beyond the glans of the penis. The central opening and the said one end of the sheath have complementary attachment components whereby the sheath may be attached to the base. The second end of sheath includes an opening and attachment means for attaching the sheath to a drain tube. In the preferred embodiment of the invention a second sheath is disposed outboard of the first sheath and secured to the base in a similar manner, the second sheath including an outer end with an opening through which the drain tube may be passed. This protects the first sheath and penis from contamination.

A coupler is provided between each sheath and the drain tube, whereby drain tube may be connected and disconnected from the sheath or sheaths without disturbing the installation of the catheter. The attachment means for the sheath to the base is selectively detachable, to accommodate examination and maintenance. One exemplary form of attachment is a Ziploc-type fastener. Another exemplary form of attachment is a Velcro-type fastener. It is desirable that the coupler for the drain tube includes a check valve assuring one-way flow in the drain tube.

A Ziploc-type allows to open system and secure a primary sheath at tip as shown in FIGS. 9 and 10.

The penile tube is connected directly to the body in the pelvic area with the tube extending therefrom to receive and house the penis. The penis is not interfered with in any manner and is simply "housed" in the penis tube. This minimizes discomfort for the user. The penis tube may be double sheathed to protect against contamination.

In certain applications, the external catheter of the subject invention may be used in combination with an in dwelling catheter which may be removed and replaced with the external release tube of the invention. This is particularly useful when an in dwelling catheter may be required immediately after surgery, for example, but could be removed after a short time even though the wearer remains incontinent. This permits long term use of a urine collector without exposing the penis to disease or infections such as sepsis, contrary to the issues common to in dwelling catheters.

In the preferred embodiment the external male catheter includes an adhesive base which has a central opening for permitting the penis to extend through the base. The base has an adhesive back, or may be made of a duoderm material which sticks to the skin. The base is attached directly to the skin in the pelvic area and completely surrounds the penis.

The central opening includes a sealing edge, such as a Ziploc type seal, for receiving the connective end of the penis tube or sheath. This permits the penis to be housed in the tube and the tube to be connected to the base.

It is desirable that the penis be double sheathed to protect against infection or contamination. In this case, a second, generally concentric sealing edge is provided in the base for a second or outer sheath or tube.

At the outer end of each sheath is a release outlet for releasing urine from the penis tube. The release outlet may be connected to a standard type catheter tube by a clip or similar means. The catheter tube then drains into a collection bag. An advantage to the subject invention is the ability to remove the collection tube and bag from the penile sheath without disturbing the catheter installation.

The removable seal between the base and each sheath permits removal of the catheter from the penis without requiring reinstallation, greatly enhancing examination and hygiene management of the penile area.

In another embodiment, the urine collection device comprises a condom catheter and urostomy pouch. Advantageously, this device may further be connected to a bedside or other drainage device.

DETAILED DESCRIPTION

Figure 1:
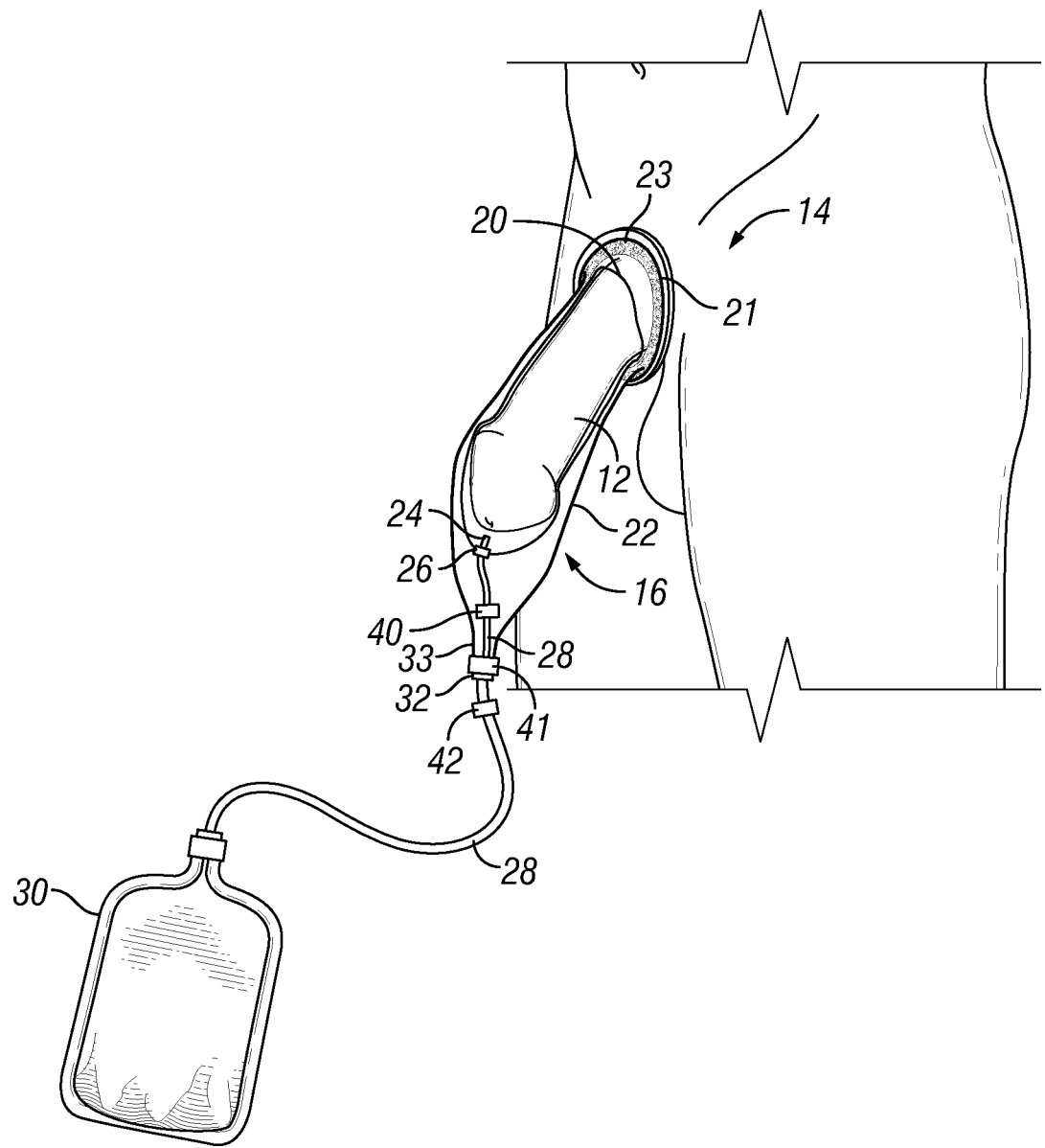
FIG. 1 is a diagrammatic view of the external catheter of the subject invention.

Referring generally to FIG. 1, the external male catheter of the subject invention is designed to be attached to a drain tube 28 of a standard catheter, with the catheter being non-invasive of the penis. The catheter includes a base 18 secured to the pelvic area 14 of a wearer, the base having a central opening 20 for accommodating a penis. Connected to the base is a sheath 22 for housing the penis, one end of the sheath adjacent the base 18 and a second end of the sheath extending beyond the glans of the penis. The central opening and the said one end of the sheath have complementary attachment components whereby the sheath may be attached to the base. The second end 24 of sheath includes an opening and attachment means for attaching the sheath to a drain tube 28. In the preferred embodiment of the invention a second sheath 25 is disposed outboard of the first sheath and secured to the base in a similar manner, the second sheath including an outer end 32 with an opening through which the drain tube may be passed. This protects the first sheath and penis from contamination.

One or more couplers 40, 41 and 42 are provided between each sheath and the drain tube, whereby drain tube may be connected and disconnected from the sheath or sheaths without disturbing the installation of the catheter. The attachment means for the sheath to the base is selectively detachable, to accommodate examination and maintenance. One exemplary form of attachment is a Ziploc-type fastener. Another exemplary form of attachment is a Velcro-type fastener. It is desirable that the coupler for the drain tube includes a check valve assuring one-way flow in the drain tube.

FIG. 1 is an illustration of the invention and shows a human body 10 with a penis 12 extending from the pelvic area 14. The subject invention is directed to an external male catheter 16 which is used with the penis 12. A base 18 includes a central hole or opening 20 large enough to permit the penis to pass freely through the base in a non-interfering manner. The back side of the base either is made of or includes an adhesive material that will attach the base directly to the skin of the wearer. A duoderm material is one suitable choice, but other adhesive devices may be employed as a matter of choice.

The central penis accommodating hole or opening 20 includes a rim 21 designed for attaching the penis sheath 22. The penis sheath loosely accommodates and encases the penis 12. The rim and end of the sheath have an attachment means such as a Velcro-type system of a Ziploc-type system for detachably securing the sheath to the base. The outer end 24 includes a release opening, such as a nipple 26 to which a catheter drain tube 28 may be attached either directly or through a series of couplers as will be described. The drain tub then empties the catheter into the collection bag 30, in the normal manner.

It is desirable to include a second sheath 25 outside the penis sheath 22 for sanitary purposes. The second sheath 25 is connected to the base by a connection element in a ring 23 outboard of the inn rim 21. In this application the outer tip 32 includes a release pro for accommodating the catheter discharge tube. The discharge tube is typically made of multiple sections with couplers 40, 41 and 42 to permit removal of bag 30 from the system without disturbing the penis encasing catheter. The couplers also facilitate installation and removal of each sheath for examination and maintenance purposes. The couplers may include one-way check valves to assure urine flow away from each sheath and the penis.

The external catheter of the invention provides a comfortable method and apparatus for applying an external catheter to a penis without leakage and with a minimum of discomfort and maintenance.

Additional Embodiments

Figure 3:
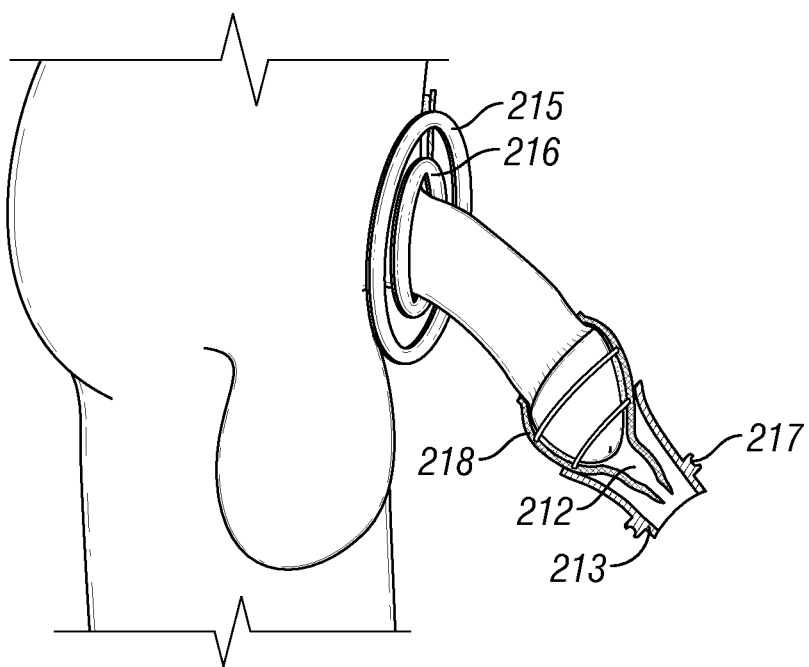
FIG. 3 shows additional embodiments including a snap ring of a urine collection device.

FIG. 3 shows another embodiment of a urine collection device. While FIG. 3 is shown as a male device one of ordinary skill in the art will appreciate that it can be readily adapted for use on a female user. Typically, the device includes an anchor mechanism 200 which may be any suitable mechanical or chemical mechanism to releasably attach the device to the wearer. Such mechanisms, include, for example, medically acceptable tape and/or other releasable adhesives such as a hydrogel, colloid, hydrocolloid, or other adhesive such as DUODERM™ and the like. Such material may often be capable of staying on a user for up to 7 days or more as an anchor and may be released at any convenient or desired time.

Figure 2:
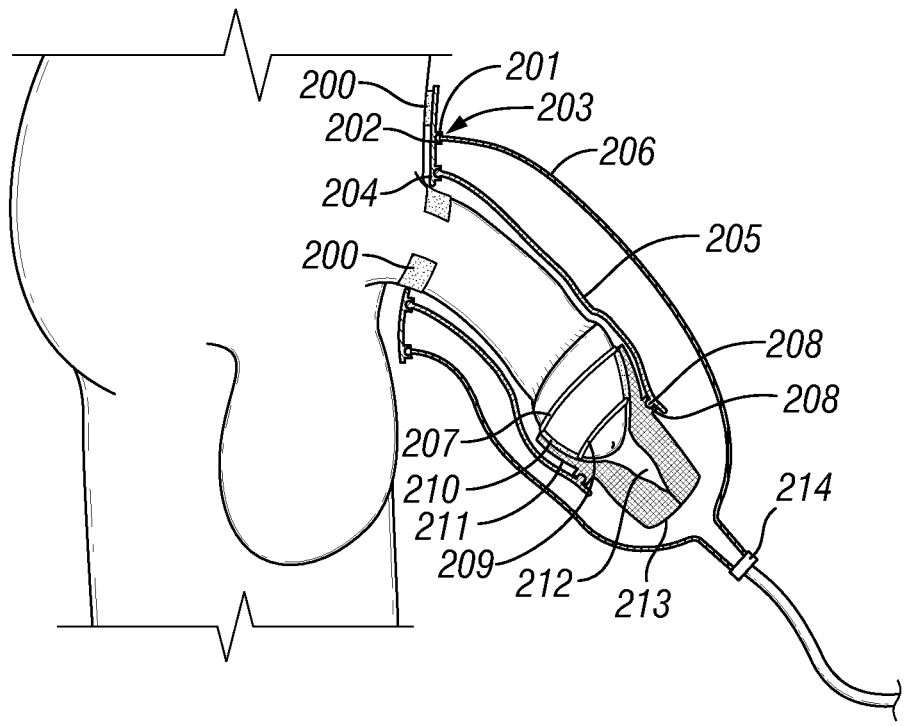
FIG. 2 shows additional embodiments including a flutter guard cylinder of a urine collection device.

In some embodiments a zip lock mechanism shown as 201-204 of FIG. 2 may be employed to attach the device from the user to a primary sheath 205 and/or an associated pouch 206. If desired a compression ring 207 and associated receiver 208 may be employed near an upper portion of the device to provide a seal and prevent or minimize urine backflow. Similarly, a lower compression ring 209 may also be additionally or alternatively employed. An adhesive or tape as described above for 200 may be employed at 210 at or near umbrella 211 which may also include an integral or separate flutter valve 212. Of course, other attachment mechanisms such as magnets or other medically acceptable attachments may alternatively be employed at 210 or at other points. Such magnets may in some circumstances increase circulation and prevent infections. A flutter valve guard cylinder 213 and/or an anti-reflux valve 214 may be advantageous in some embodiments.

If employed, a flutter valve guard cylinder 213 may be constructed of any appropriate size and appropriate material. Such cylinders may facilitate protection of the flutter valve from damage or malfunction due to, for example, patient movement and the like. The guard cylinder may be substantially cylindrical or another shape and is preferably as short as 0.25 inches in length and constructed of, for example, silicon or other readily injectable molded material. Typically, the cylinder is relatively rigid to prevent damage to or kinking of the flutter valve if the guard is deformed or bent.

FIG. 3 shows other potential embodiments of the urine collection device. Specifically, FIG. 3 depicts an embodiment wherein snap rings 215 attach to a base and potentially fasten to 200 porous adhesive, tape, magnets, or alternatively to snap ring 216 which can snap or adhere to primary sheath 205. A ring channel 217 may snap end of primary sheath 205 to seal distal end of sheath if desired. If desired a helmet 218 may be adhered over DUODERM and/or snapped onto compression ring 207, 208, or both.

Figure 4:
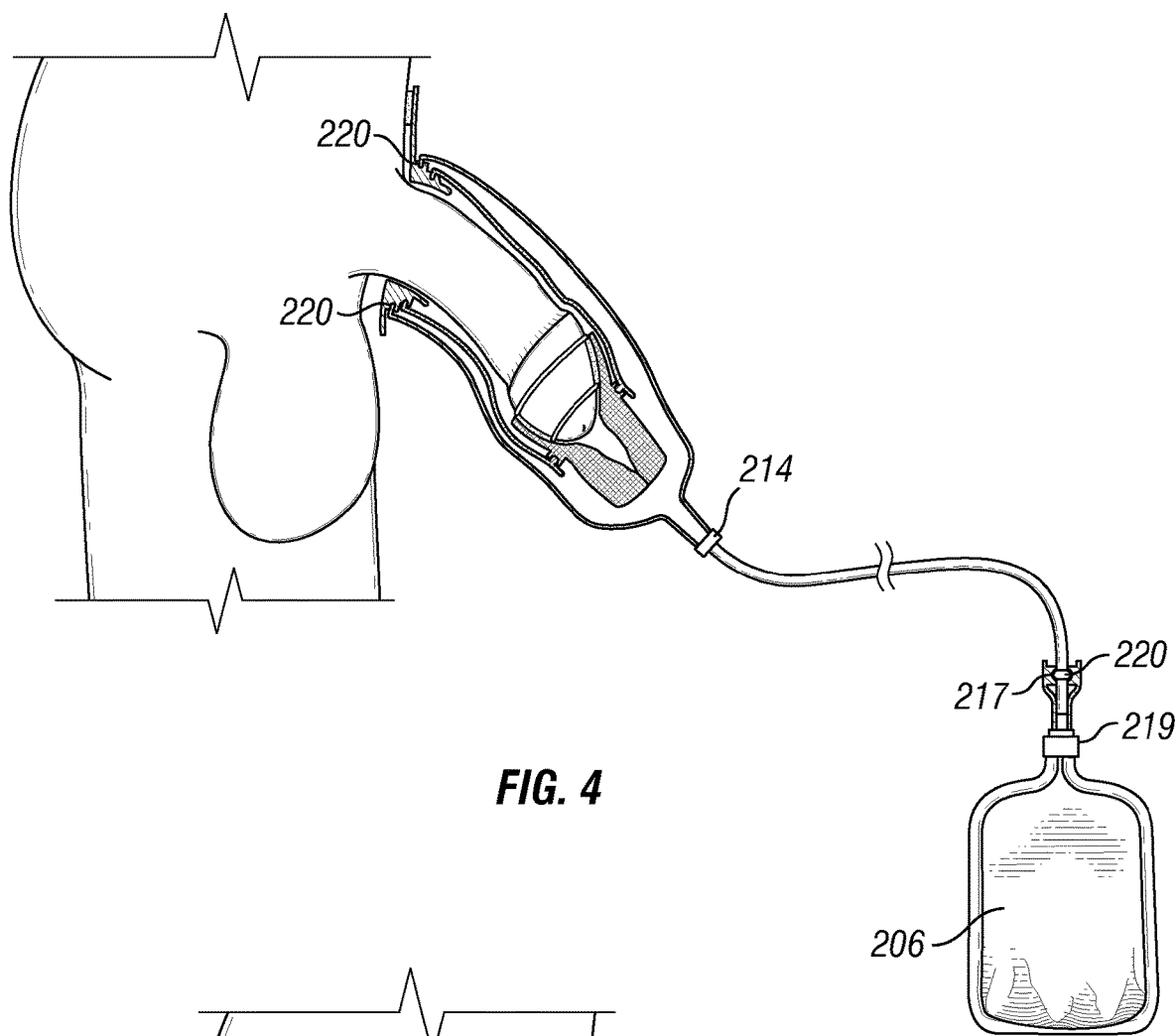
FIG. 4 shows additional embodiments including a snap ring bead fitting into ring channel of a urine collection device.

FIG. 4 shows additional embodiments. For example, there may be a second anti-reflux valve 219 located distal to the anti-reflux valve 214. In addition, ring channel 217 near an end of pouch 206 may be attached in any convenient manner to a snap ring bead 220.

Figure 5:
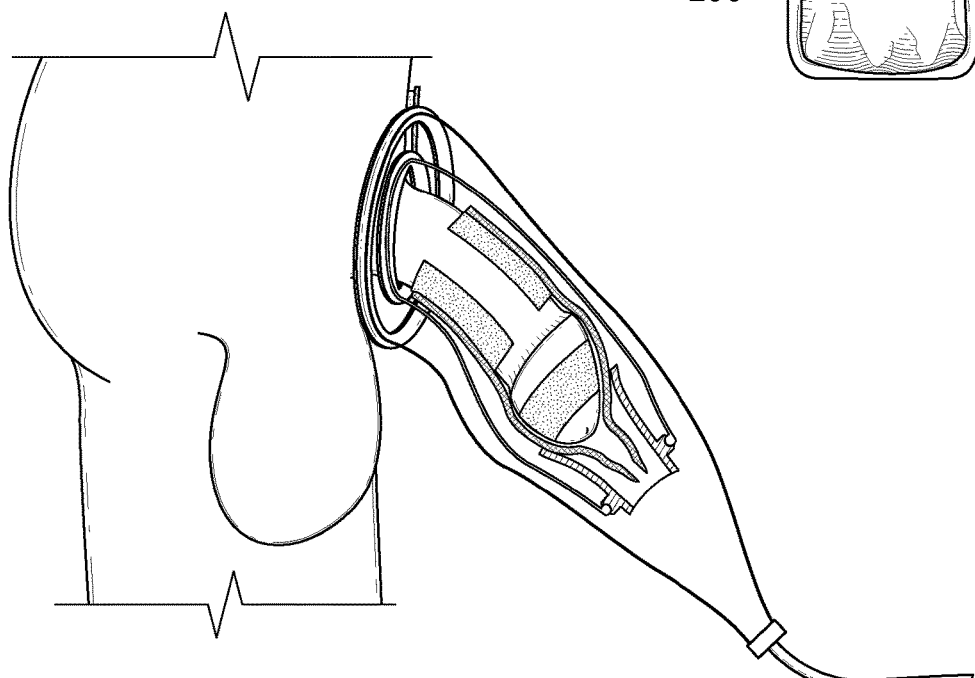
FIG. 5 shows a urine collection device in use.

FIG. 5 shows a representative embodiment wherein a urine collection device is in use with urine collected and stored outside and away from sensitive areas.

Figure 6:
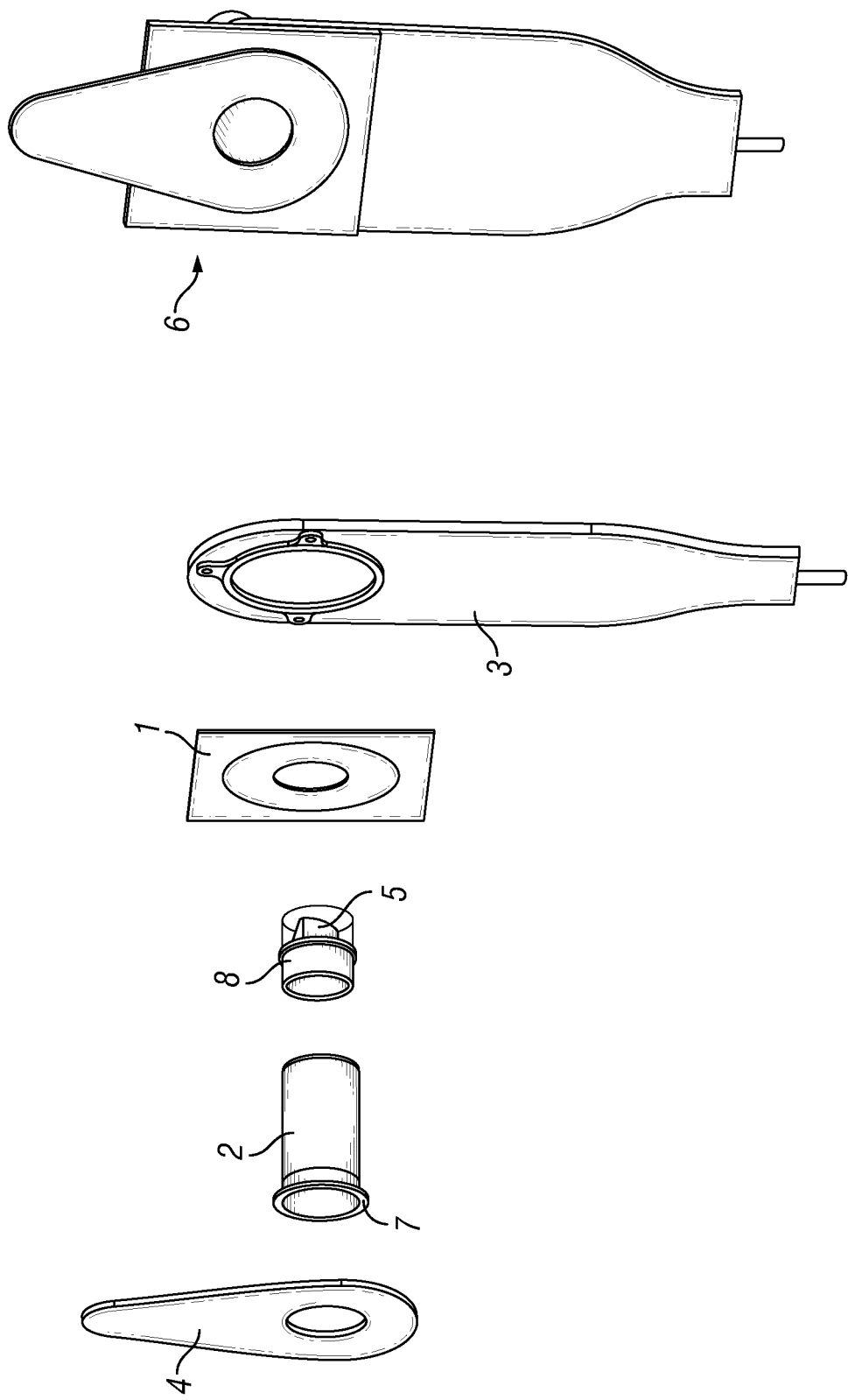
FIG. 6 shows components of a urine collection device embodiment.

FIG. 6 shows specific embodiments of a urine collection device 6. In this embodiment a belly button anchor 4 and sheath 2 are configured to be attached to one another via a lip 7 at the proximal portion of the sheath nearest the intended user. Of course, if desired a belly button anchor and sheath may be integral.

The belly button anchor 4 may be made of any convenient material such as a flexible or rigid plastic or polymer. The sheath is preferably a flexible material that can be rolled on an intended user such as that used in condoms, e.g., latex, polyurethane, polyisoprene, nitrile, or lambskin. The belly button anchor side opposite the sheath side may have an adhesive or other manner of connecting the top of the belly button anchor near a user's belly button. In this manner a secure attachment is made for the device which facilitates preventing leakage as the user goes about daily activities.

A one way valve 5, for example, a flutter valve is configured to be attached or may be made integral with the distal end of the sheath. The valve 5 is protected by a cap or helmet or guard cylinder 8. Typically, such a cap or helmet or guard cylinder 8 is comprised of a relatively rigid, non-bending material and configured to prevent damage to the one way valve 5. Such materials include, for example, injection molded silicon.

The size of the cap or helmet or guard cylinder 8 varies depending upon the size of the valve but often the length may range from ⅛ inch to ½ inch and is preferably ¼ inch in some embodiments. The cap or helmet or guard cylinder 8 surrounds the valve to protect it but is at least partially open or has an aperture at the distal end so that urine may exit the flutter valve travel through the opening in lock ring 1 and into the reservoir 3.

In some embodiments lock ring 1 and reservoir 3 are configured to be releasably attached to one another. Lock ring 1 has an opening such that at least a portion of the valve 5 with cap or helmet or guard cylinder 8 may fit within the opening on lock ring 1. In some embodiments the cap or helmet or guard cylinder 8 is tightly fit within the opening on lock ring 1. That is, the circumference of the opening on lock ring 1 is nearly the same or only slight larger than that of the cap or helmet or guard cylinder 8. Of course, the opening of lock ring 1 may be a shape other than a circle in which case it may advantageous to have the shape of the cap or helmet or guard cylinder 8 match that of the lock ring 1.

In sum, the embodiments n FIG. 6 allow a urine collection device 6 to be attached to a user at or near a belly button via belly button anchor 4. In practice urine may then go through the flutter valve 5, lock ring 1, and into the reservoir 3. The reservoir 3 may be detached when it is at least partially full and replaced so that the urine collection device may be used repeatedly.

The reservoir 3 may be of any convenient material, size, and shape. In some embodiments the material is a plastic like polyethylene, polypropylene, silicon, latex, polyurethane, polyisoprene, nitrile, lambskin or other materials. The reservoir 3 may have multiple compartments and/or may have one or more valves inside. In some embodiments the reservoir may be configured to connect to another reservoir through a tube located at a convenient location such as at the bottom.

Figure 7:
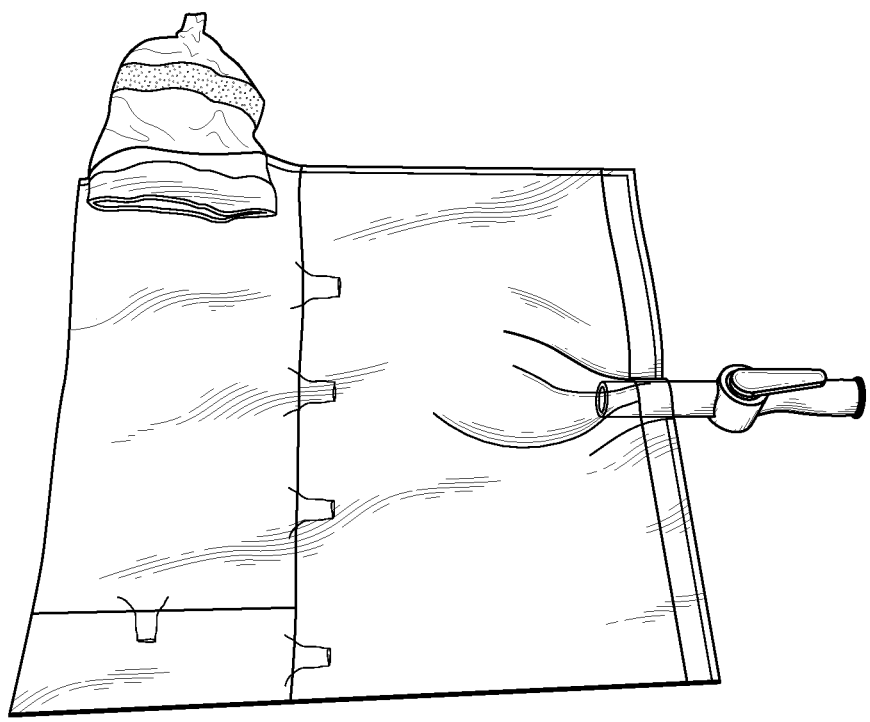
FIG. 7 shows components of a urine collection device embodiment.
Figure 8:
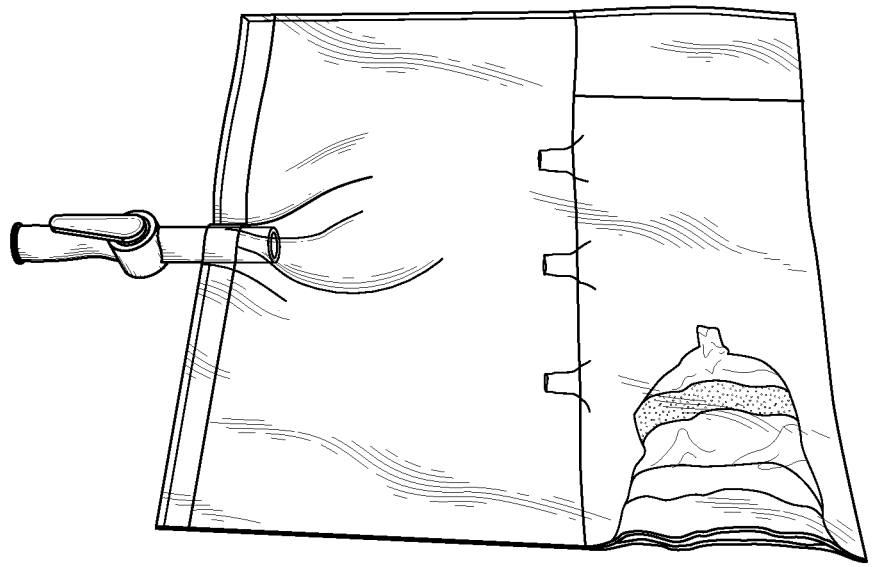
FIG. 8 shows components of a urine collection device embodiment

FIGS. 7 and 8 shows additional or alternative potential embodiments wherein a sheath may be configured to invert into a pouch wherein one or more valves such as flutter valves are located along the sheath such that urine may flow from the sheath through the valves into the valves. As in the other embodiments described above a hydrogel or other adhesive may be employed to attach to the glans of a penis.

Figure 9:
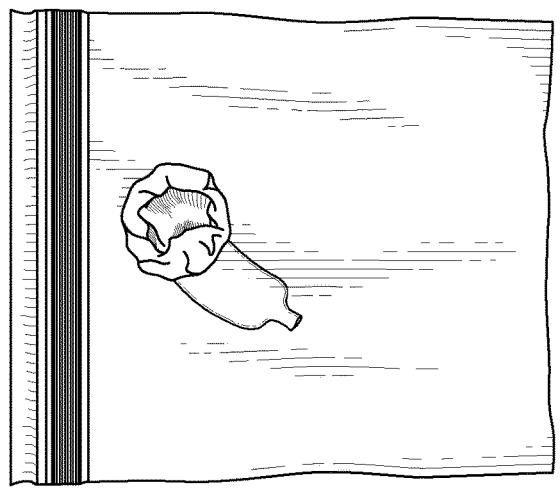
FIG. 9 shows a Zip-lock-type feature.
Figure 10:
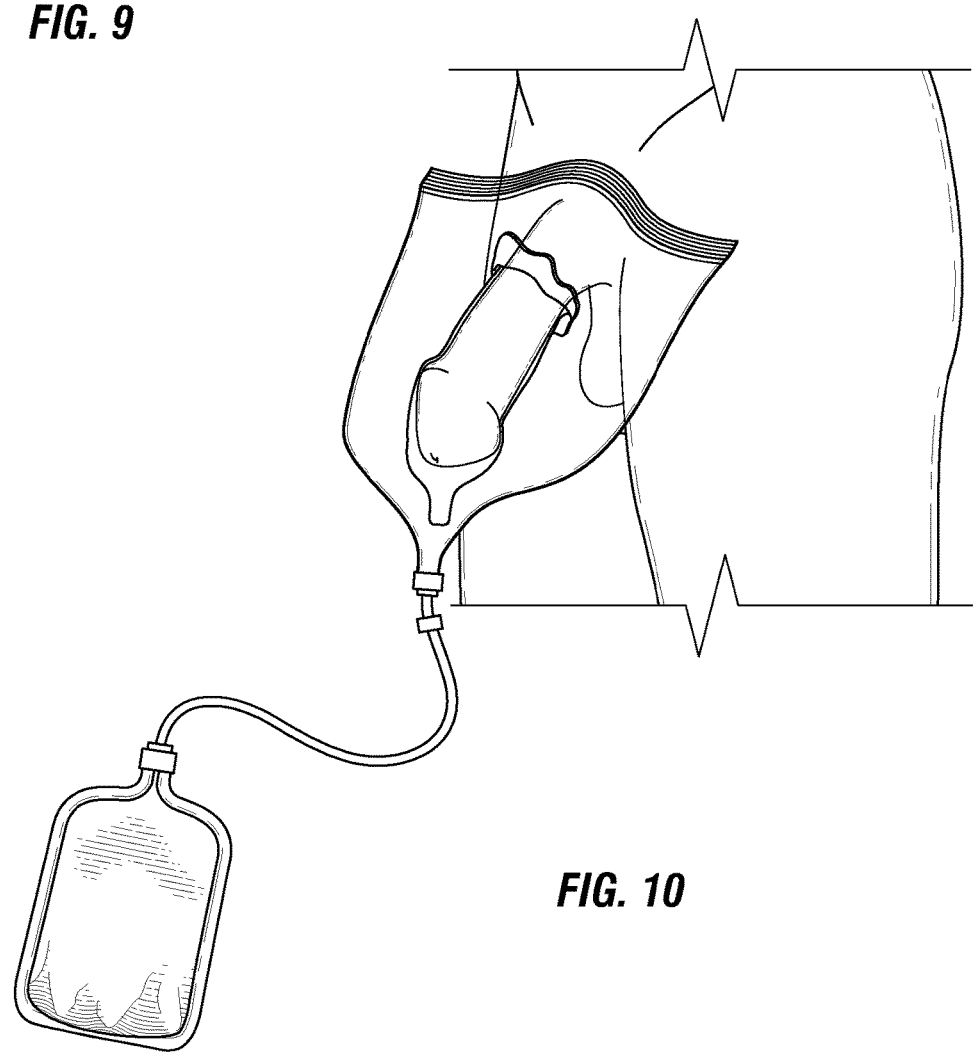
FIG. 10 shows an alternative view of a Zip-lock-type feature.

FIGS. 9 and 10 show additional embodiments associated with a Ziplock-type fastener with a primary sheath.

Figure 11:
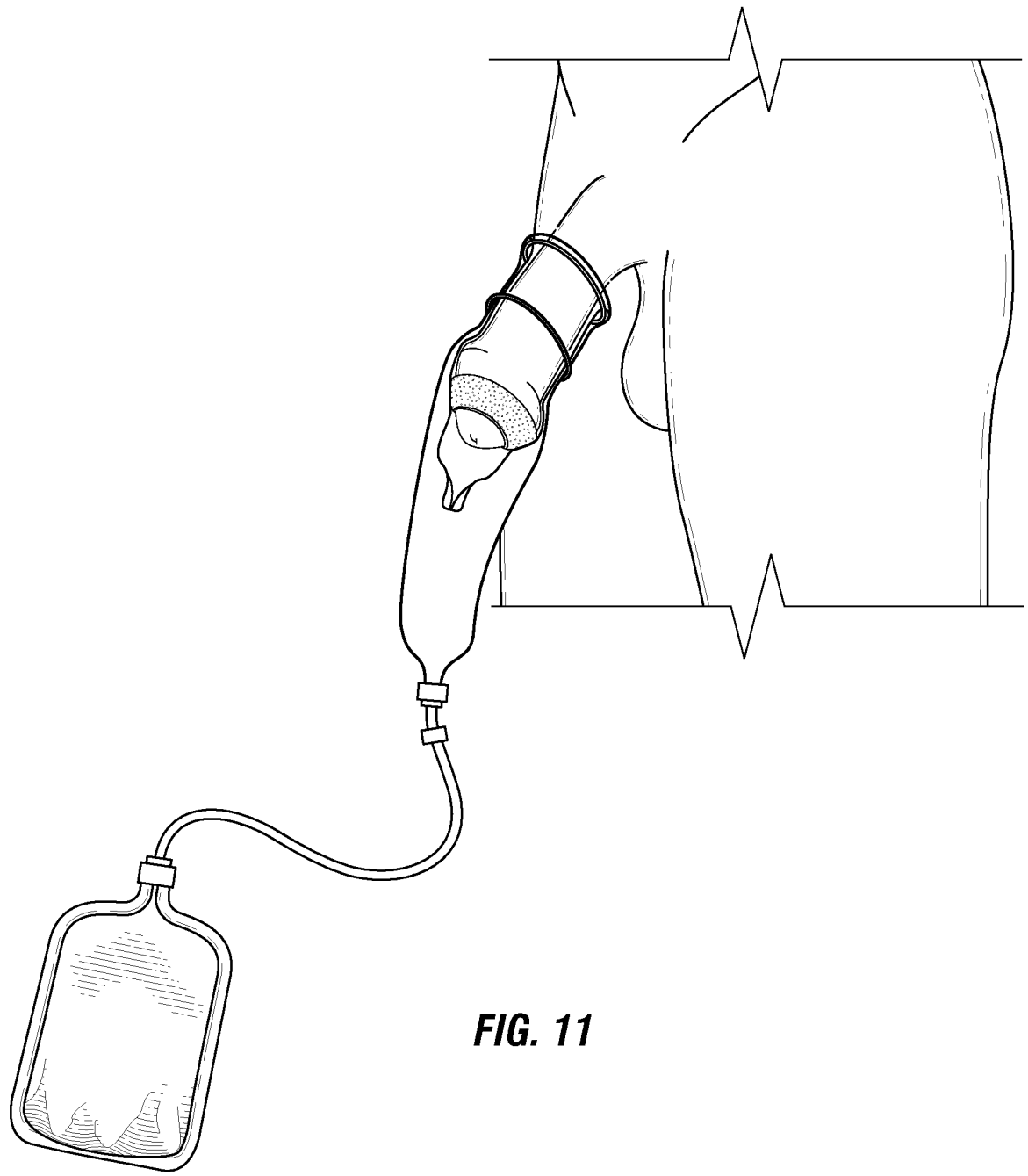
FIG. 11 shows an embodiment with two sheaths and an anti-reflux valve.

FIG. 11 shows a secondary sheath, i.e., tube, rolled over the primary sheath with or without a flutter valve. If desired, the apparatus may be anchored in or around a user's belly button. Advantageously, a good seal may be provided between the mietus and an exit port for the urine from the sheath. This embodiment is somewhat similar to that described in application Ser. No. 16/387,069, filed Apr. 17, 2019 which is incorporated herein by reference except that in this embodiment there are two separate sheaths adhered together.

Figure 12:
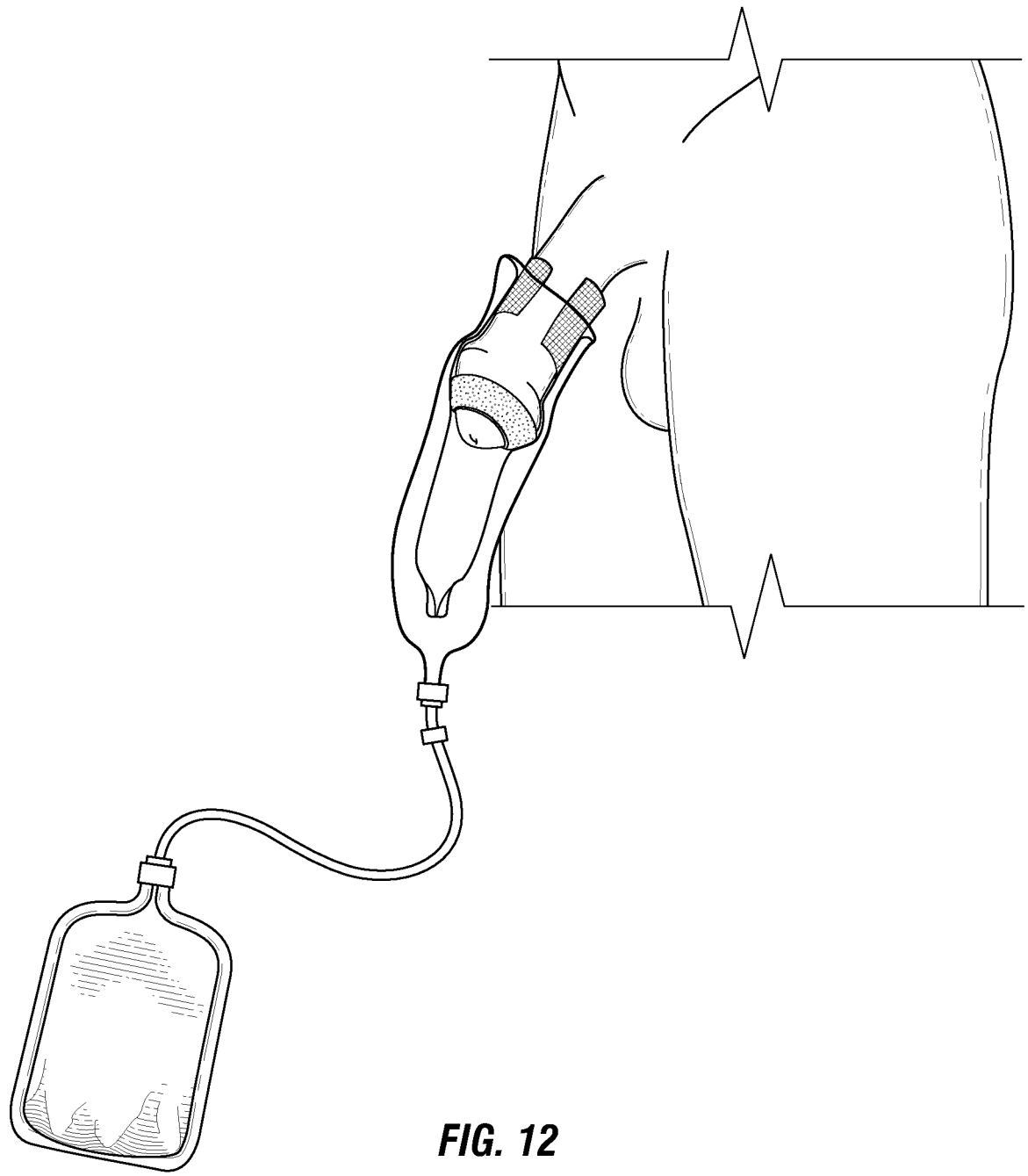
FIG. 12 shows an inverted primary sheath embodiment.

FIG. 12 shows adhesive, kellum grip, magnets or some other attachment mechanism employed to hold the sheaths together. A flutter is shown which may or may not also have a guard integral or attached.

Figure 13:
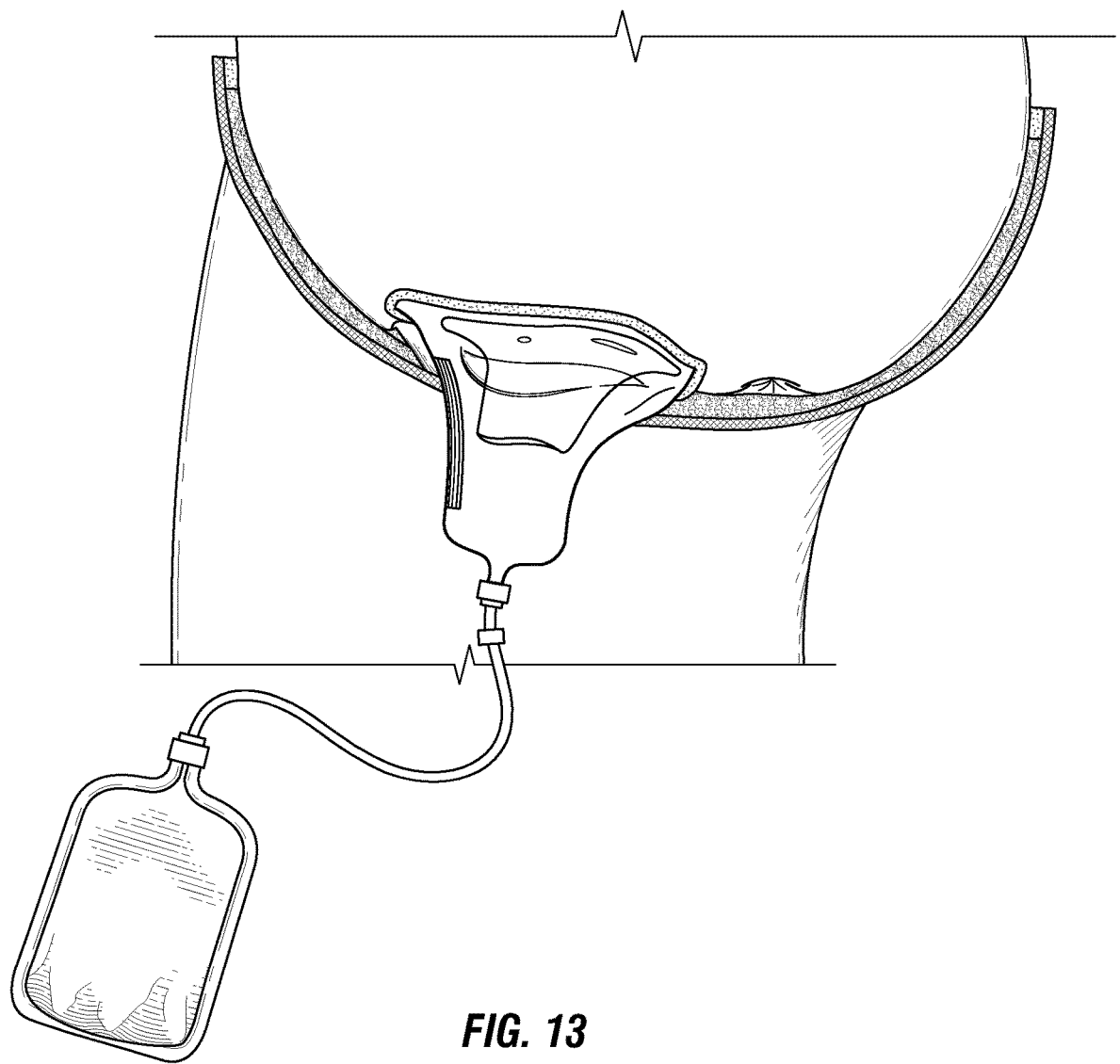
FIG. 13 shows an embodiment with a wicking anchor.

FIG. 13 shows a wicking material which may be any suitable material including, for example, a superabsorbent polymer such as those employed in diapers. An antiseptic cloth or other cleaning mechanism may be releasably attached via Ziplcok-type attachment, Velcro, magnet strips, or other mechanism. If desired an irrigating device may alternatively or additionally be releasably attached to hold HIBICLENS or other antiseptics. In this manner the use may clean the apparatus so that it may be employed longer with a reduced risk of infection. The apparatus may be sized to fit a particular user and also may be configured as a menses device.

Figure 14:
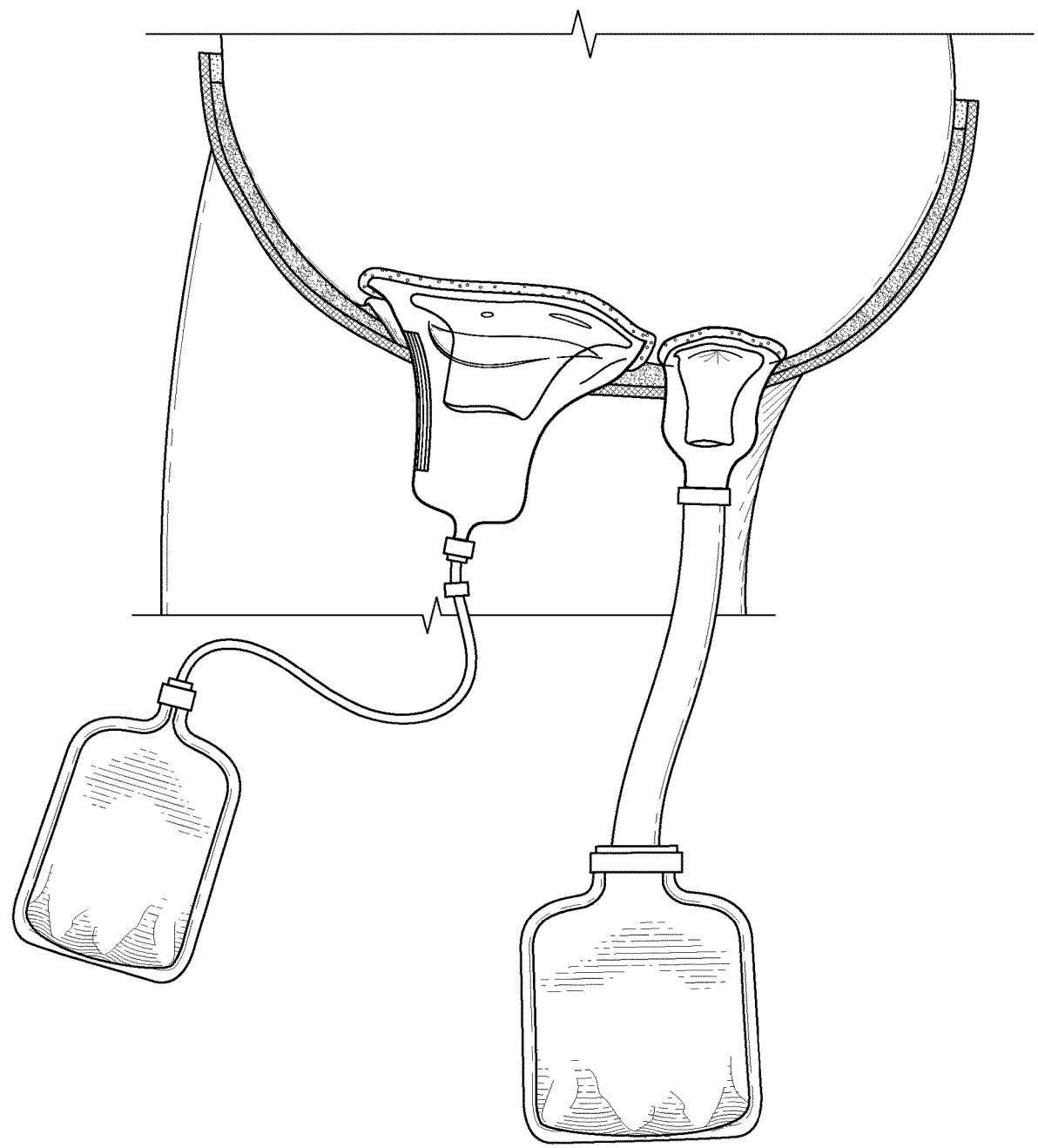
FIG. 14 shows an embodiment with a fecal pouch.
Figure 15:
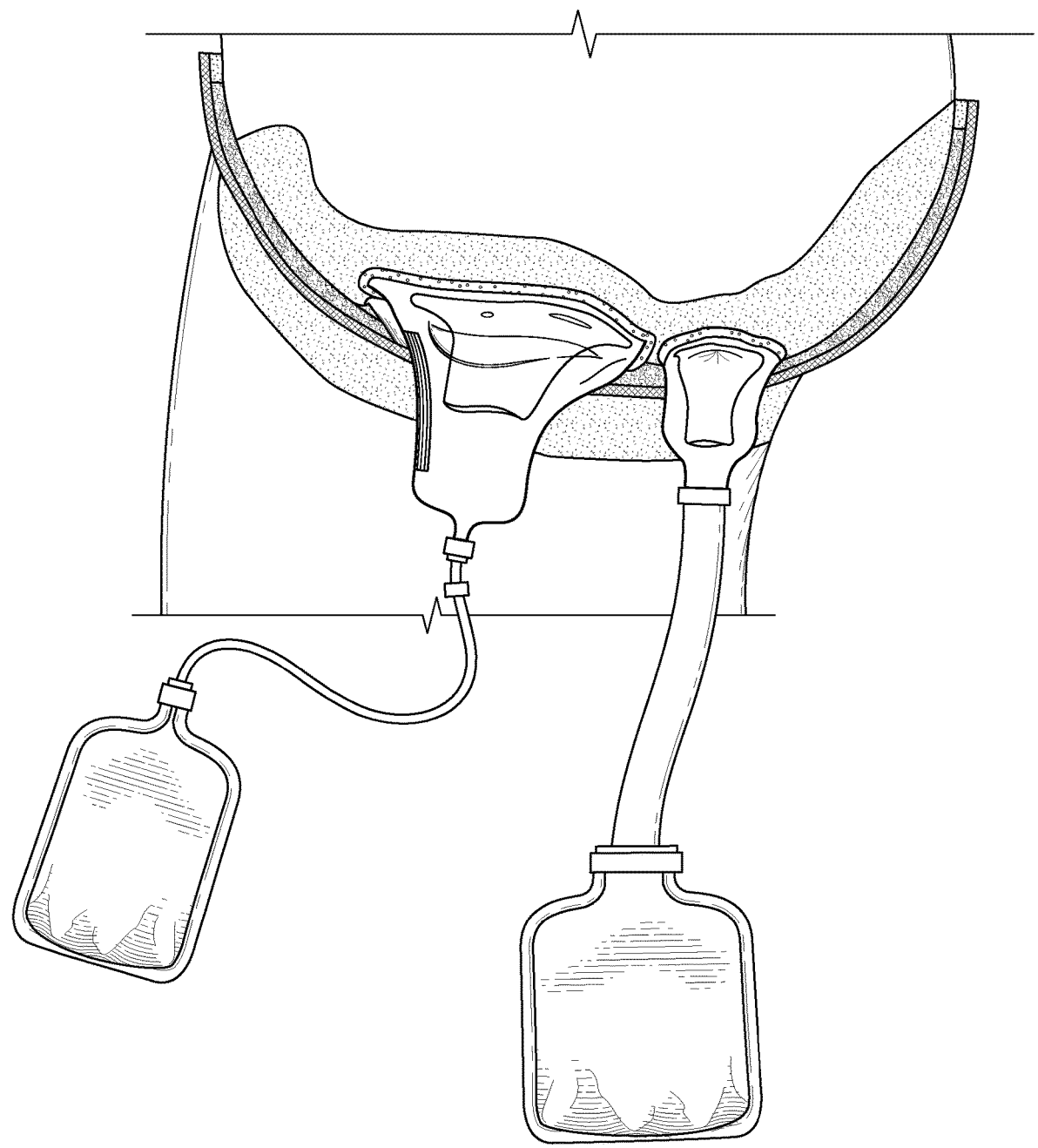
FIG. 15 shows an embodiment with a wicking material.

FIG. 14 shows an apparatus with an optional diaper anchor and fecal pouch while FIG. 15 shows the apparatus with TAGADERM or another adhesive which may include an antimicrobial such as silver or copper, a hydrogel, honey, or any suitable medication to assist in potential healing. Bedside drainage devices are shown at the bottom of the figure that may be employed.

Figure 20:
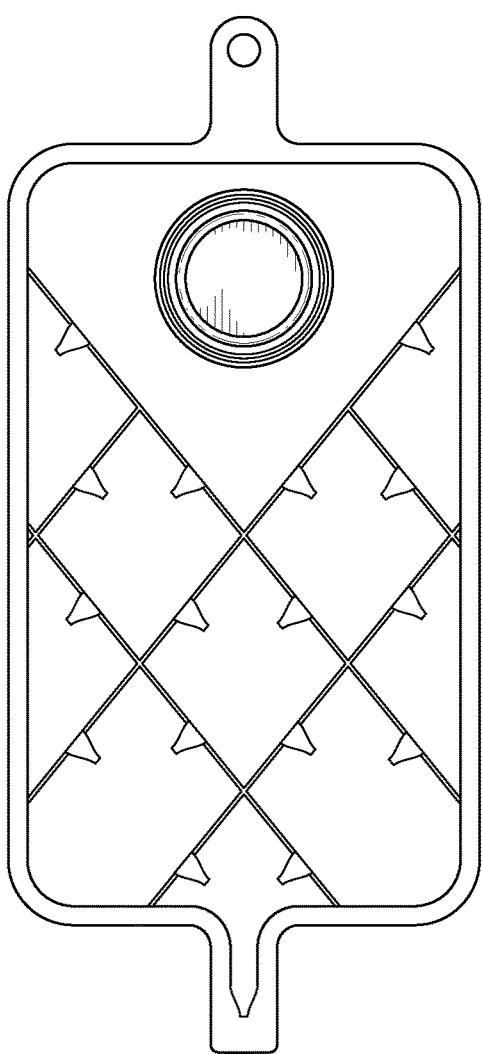
FIG. 20 shows an embodiment wherein a urine pouch has a zip-lock type (retentive tongue and groove) fastener, a series of one way valves and separate compartments.

FIG. 20 represents specific urine collection device, e.g., pouch, embodiments that may be employed. A ziplock-type fastener (retentive tongue and groove) may be employed to connect the pouch to any of the sheaths or condom catheter described above via, if desired, a drain tube. Alternatively, the ziplock-type fastener may attach the pouch to another pouch such as a primary pouch via, if desired, a drain tube. The pouch may have a series of one way valves connecting a plurality of separate compartments within the pouch. A drain tube may have the one way valve depicted in FIG. 20 to allow urine to enter the pouch and prevent urine from exiting the pouch. Advantageously, the separate compartments, if employed, serve to have an anti-slush or anti-slosh effect wherein urine does not slosh around within the pouch as a user moves, but rather, is contained within the smaller separate compartments. The separate compartments also may prevent free flow within the pouch and prevent the pouch from bursting if a user puts some weight on the pouch. The plurality of compartments may be any size or shape and in some embodiments are diamond-shaped. The material of the pouch is generally flexible and water-proof such as rubber, latex, elastomers, polyurethane, polyisoprene, nitrile, lambskin, polymers and the like as may be used for the condom catheter and urine collection devices described above.

Figure 21A:
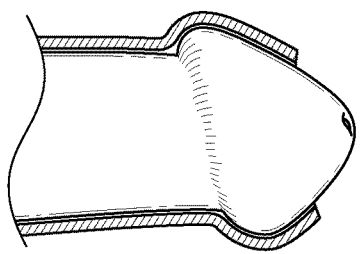
FIG. 21A shows embodiments wherein a sheath is configured to be anchored around and over a corona of glans with or without adhesive.

FIG. 21A shows a sheath constructed of very elastic stretching and the sheath may have a thinner area configured to go around and over corona of penis and be anchored to hinder and/or prevent substantial or any urine leakage with or without adhesive. In this manner the sheath may fit similarly to a sock over a foot.

Figure 21B:
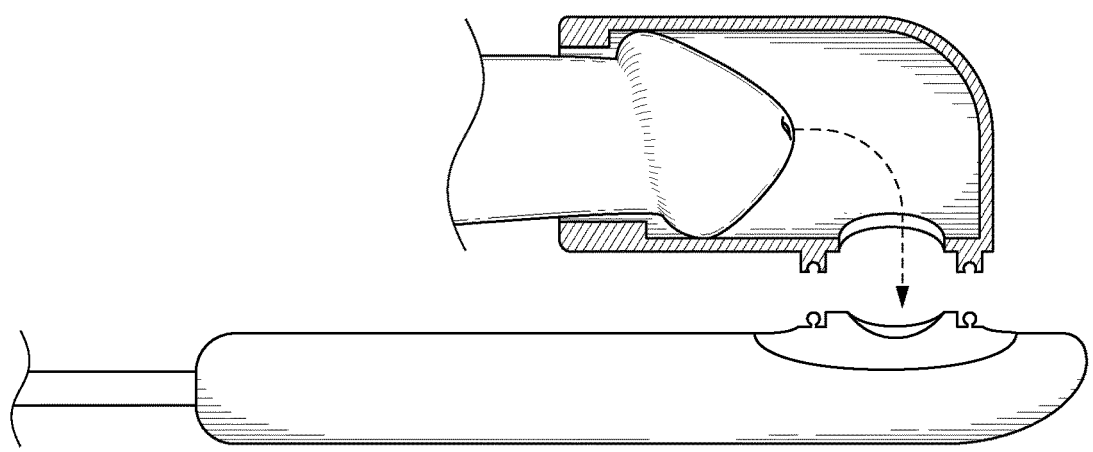
FIG. 21B shows embodiments wherein a sheath and urine pouch operably connected via urine drain port are configured to be connected via a ziplock-type male and female connector.
Figure 22:
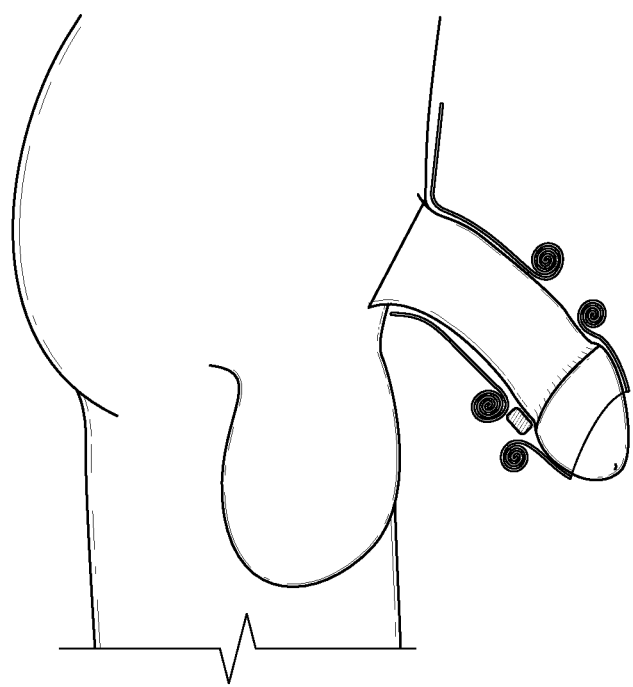
FIG. 22 shows various sheath embodiments.

FIG. 21B shows embodiments wherein a sheath and urine pouch operably connected via urine drain port are configured to be connected via a ziplock-type male and female connector. In some embodiments the may be configured such that the penis is out of pouch but has a flutter valve free flowing into pouch similar to a condom catheter slightly penetrating an ostomy pouch similar to the embodiments further described below with respect to FIGS. 16-19.

Figure 16:
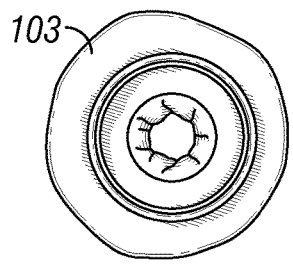
FIG. 16 shows a disassembled two piece urostomy pouch.

FIG. 16 shows a conventional two piece urostomy pouch although a one piece pouch may also be employed. Such pouches are commercially available from companies such as Hollister and other medical device companies. They typically comprise the pouch 100 which has a valve 101 on one end with an opening 102 on the other end. The opening is designed to have a cap 103 to be sealed on it in some manner to prevent fluid leakage.

Figure 17:
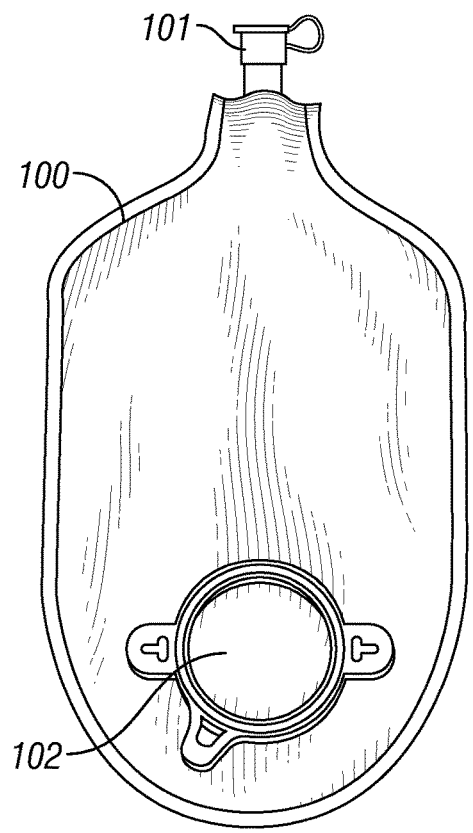
FIG. 17 shows an assembled two piece urostomy pouch.
Figure 17:
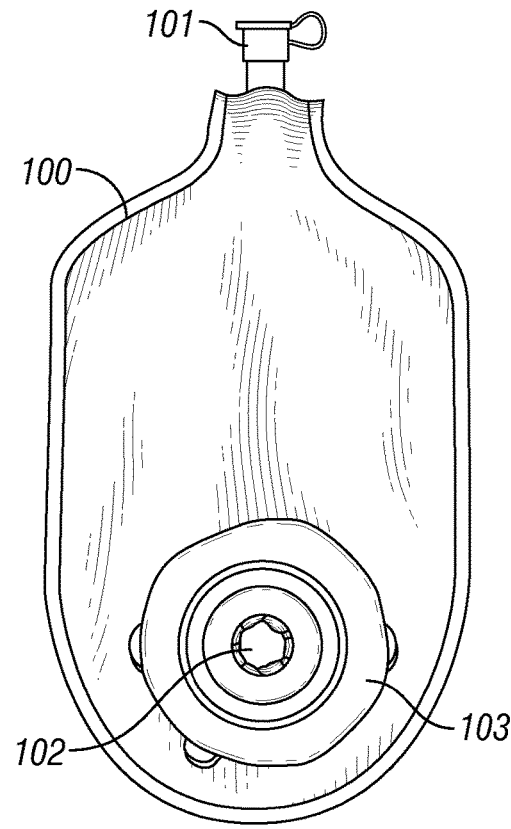

FIG. 17 shows an assembled two piece urostomy pouch wherein the cap 103 is sealed to the pouch 100 via a snapping or other seal mechanism. A cap opening 104 is designed so that a stem 201 of a condom catheter 200 may be fit within or affixed to the opening 104 in a leak proof manner.

Figure 18:
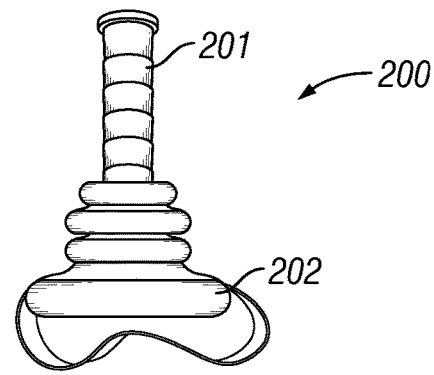
FIG. 18 shows a condom catheter.
Figure 19:
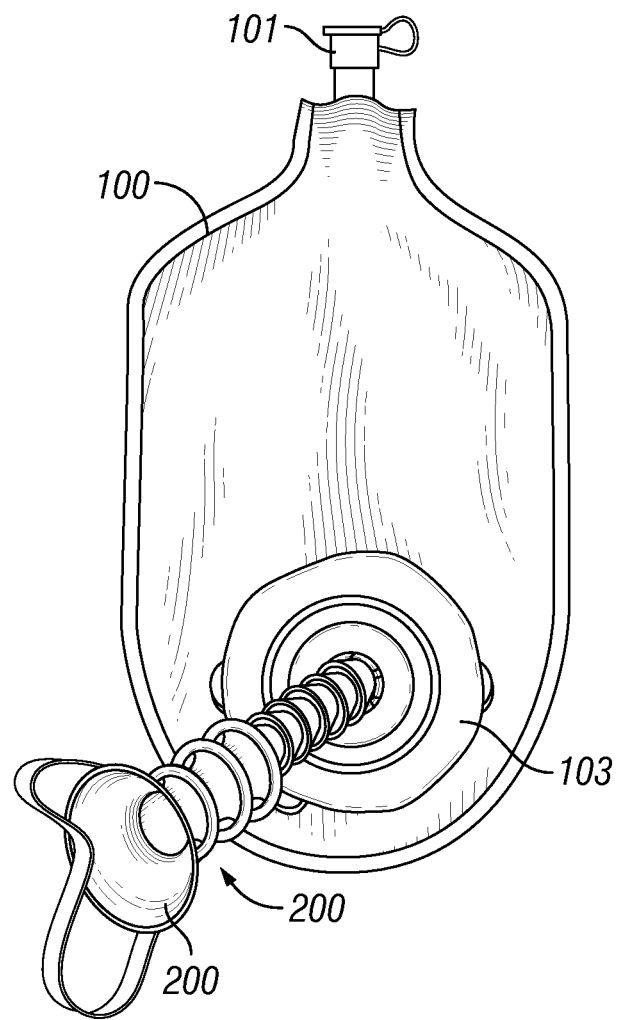
FIG. 19 shows a device of the present invention employing the two piece urostomy pouch and condom catheter.

FIG. 18 shows a condom catheter 200 having a stem 201 opening to a rolled condom 202 while FIG. 19 shows the stem 201 of the condom catheter partially inserted into the cap opening 104 of the urostomy bag. The stem may comprise a one way valve if desired. To complete the device the stem would be sealed tightly in a convenient manner within the cap opening so at to prevent leakage. The user would then roll condom 202 over at least a portion of the shaft of his penis. If desired, at least a portion to all of condom 202 may be ventilated with perforations or some other manner to provide ventilation. That is it may be rolled past glans, past corona, and/or to mid shaft. If desired the condom may be affixed with suitable adhesive such as hypfix tape to secure the condom on the penis. The valve 101 may be connected to a bedside collection device if desired. If desired, the pouch may be affixed under or near the navel. Alternatively, a strap may extend around the user's waist affixing the pouch securely.

In an alternative embodiment, instead of a pouch with a valve only the opening 102 with base around it is employed. A cylindrical sheath is passed through the opening in both front and back. In this manner the penis may be inserted into the sheath through the opening and the sheath may be affixed to the penis as described above and the end of the sheath is closed to collect urine. As with the condom above the sheath that is affixed to the penis may be perforated to provide ventilation to the glans, corona, and/or shaft.

In sum, in certain embodiments of FIG. 16-19 the device pertains to a urine collection device comprising: a urostomy pouch having an opening; and a condom catheter having an opening; wherein the opening of the condom catheter is inserted into the opening of the urostomy pouch in a substantially leak proof manner. In other embodiments, individual features of various figures may be combined.

While certain features and embodiments have been described in detail herein, it should be understood that the invention encompasses all modifications and enhancements within the scope and spirit of the following claims.

The invention claimed is:

1. A collection device comprising:
   an anchor designed to be secured near a pelvic area of a user, the anchor comprising a central opening;
   a sheath having a proximal end and a distal end, the proximal end of the sheath designed to be in contact with and attached to the anchor around the central opening and the distal end of the sheath comprising an opening with a valve and a surrounding helmet with an aperture located at the opening, wherein the helmet is configured to be connected to a lock ring with a releasably attached urine reservoir; and at least a portion of the valve fits within an opening on the lock ring.

2. The collection device of claim 1 wherein the valve is a flutter valve.

3. The collection device of claim 1 wherein the sheath comprises latex, polyurethane, polyisoprene, nitrile, lambskin, or a mixture thereof.

4. The collection device of claim 1 wherein the reservoir comprises a valve.

5. The collection device of claim 1, wherein the sheath is configured to be inserted into the reservoir.

6. The collection device of claim 1, wherein the proximal end of the sheath comprise release outlet.

7. The collection device of claim 1 wherein the anchor comprises is designed for attaching the sheath with a rim on the sheath.

8. The collection device of claim 1 wherein the proximate end of the sheath is designed to be releasably attached to the anchor.

9. The collection device of claim 1 wherein the proximate end of the sheath is designed to be selectively detachable to the anchor using a Ziploc-type fastener.

10. The collection device of claim 1 wherein the proximate end of the sheath is designed to be selectively detachable to the anchor using a Velcro-type fastener.

11. The collection device of claim 1 wherein the anchor is designed to be adhesively secured to the pelvic area or belly button area of a wearer.

12. The collection device of claim 1 wherein the central opening of the anchor is designed to accommodate a penis.

13. A collection device comprising:
an anchor designed to be secured near a pelvic area of a user, the anchor comprising a central opening;
a sheath having a proximal end and a distal end, the proximal end of the sheath designed to be in contact with and attached to the anchor around the central opening and the distal end of the sheath comprising an opening with a valve and a surrounding cap with an aperture located at the opening, wherein the cap is configured to be connected to a lock ring with a releasably attached urine reservoir; and at least a portion of the valve fits within an opening on the lock ring.

14. A collection device comprising:
an anchor designed to be secured near a pelvic area of a user, the anchor comprising a central opening;
a sheath having a proximal end and a distal end, the proximal end of the sheath designed to be in contact with and attached to the anchor around the central opening and the distal end of the sheath comprising an opening with a valve and a guard cylinder with an aperture located at the opening, wherein the guard cylinder is configured to be connected to a lock ring with a releasably attached urine reservoir; and at least a portion of the valve fits within an opening on the lock ring.

15. The collection device of claim 13, wherein the valve is a flutter valve.

16. The collection device of claim 13, wherein the sheath comprises latex, polyurethane, polyisoprene, nitrile, lambskin, or a mixture thereof.

17. The collection device of claim 13, wherein the proximate end of the sheath is designed to be selectively detachable to the anchor using a Velcro-type fastener.

18. The collection device of claim 14, wherein the valve is a flutter valve.

19. The collection device of claim 14, wherein the sheath comprises latex, polyurethane, polyisoprene, nitrile, lambskin, or a mixture thereof.

20. The collection device of claim 14, wherein the proximate end of the sheath is designed to be selectively detachable to the anchor using a Velcro-type fastener.

* * * * *